United States Patent
Cupps et al.

(10) Patent No.: US 9,176,211 B2
(45) Date of Patent: Nov. 3, 2015

(54) METHOD FOR QUANTITATIVELY MAPPING MYOCARDIAL CONTRACTILE FUNCTION WITH MAGNETIC RESONANCE BASED MULTIPARAMETRIC STRAIN ANALYSIS

(75) Inventors: Brian P. Cupps, Manchester, MO (US); Michael K. Pasque, Town and Country, MO (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 901 days.

(21) Appl. No.: 12/350,444

(22) Filed: Jan. 8, 2009

(65) Prior Publication Data

US 2009/0281415 A1    Nov. 12, 2009

Related U.S. Application Data

(60) Provisional application No. 61/020,068, filed on Jan. 9, 2008, provisional application No. 61/020,060, filed on Jan. 9, 2008, provisional application No. 61/092,999, filed on Aug. 29, 2008.

(51) Int. Cl.
| | |
|---|---|
| *A61B 5/05* | (2006.01) |
| *G01R 33/563* | (2006.01) |
| *A61B 5/055* | (2006.01) |
| *G01R 33/56* | (2006.01) |

(52) U.S. Cl.
CPC .......... *G01R 33/56333* (2013.01); *A61B 5/055* (2013.01); *G01R 33/5608* (2013.01)

(58) Field of Classification Search
USPC .................................. 600/407, 410; 382/128
See application file for complete search history.

(56) References Cited

U.S. PATENT DOCUMENTS

| | | |
|---|---|---|
| 5,054,489 A | 10/1991 | Axel et al. |
| 5,217,016 A | 6/1993 | Axel et al. |
| 5,275,163 A | 1/1994 | McKinnon et al. |
| 6,171,241 B1 | 1/2001 | McVeigh et al. |
| 6,721,589 B1 | 4/2004 | Zhu et al. |
| 6,757,423 B1 | 6/2004 | Amini |
| 7,030,874 B2 | 4/2006 | Allouche |
| 2001/0031037 A1* | 10/2001 | Prince et al. ................. 378/137 |
| 2002/0176637 A1 | 11/2002 | Allouche |
| 2006/0034508 A1* | 2/2006 | Zhou et al. ................... 382/156 |

(Continued)

OTHER PUBLICATIONS

Qian et al (Ultrasound Myocardial Elastography and Registered 3D TAGGED MRI: Quantitative Strain Comparison, N. Ayache, S. Ourselin, A. Maeder (Eds): MICCAI 2007, Part 1, LNCS 4791, pp. 800-808, 2007).*

(Continued)

*Primary Examiner* — Joel F Brutus
(74) *Attorney, Agent, or Firm* — Armstrong Teasdale LLP

(57) ABSTRACT

The strain at different locations in a subject's heart is determined by acquiring a series of MR images using a tagging pulse sequence (SPAMM) that produces a grid of lines in the reconstructed images. Circumferential strain, longitudinal strain, and the minimum principal strain angle, are all calculated at locations in the heart. These raw strain values are normalized by comparing them with corresponding values in a stored reference heart model. The normalized values at each location are combined to form a composite multiparametric strain index that is indicative of myocardial contractile function and these values are employed to modulate the color at corresponding locations in an anatomical image of the subject's heart.

18 Claims, 11 Drawing Sheets

(56) References Cited

U.S. PATENT DOCUMENTS

| | | | |
|---|---|---|---|
| 2007/0118041 A1* | 5/2007 | Nishiura et al. | 600/508 |
| 2008/0077032 A1 | 3/2008 | Holmes et al. | |
| 2009/0048513 A1* | 2/2009 | Friedman et al. | 600/437 |

OTHER PUBLICATIONS

Kruijer et al (Three-dimensional Myocardial Strains at End-Systole and during Diastole in the Left Ventricle of Normal Humans, Journal of Cardiovascular Magnetic Resonance, 4(3), 341-352, 2002).*

Montillo (Automated volumetric model construction and dynamic segmentation of the heart ventricles in tagged MRI, University of Pensylvania, 2004).*

Gilliam et al (Cardiac motion recovery via active trajectory field models, Mar. 2009).*

P. Moustakidis, et al., "Noninvasive, quantitative assessment of left ventricular function in ischemic cardiomyopathy", Journal of Surgical Research, vol. 116, Issue 2, pp. 187-196.

M. J. Moulton, et al., "Spline surface interpolation for calculating 3-D ventricular strains from MRI tissue tagging", Am J Physiol Heart Circ Physiol 270: H281-H297, 1996.

Douglas Bree, et al., "Low-Dose Dobutamine Tissue-Tagged Magnetic Resonance Imaging With 3-Dimensional Strain Analysis Allows Assessment of Myocardial Viability in Patients With Ischemic Cardiomyopathy", Strain and Viability in Ischemic Cardiomyopathy, Circulation 2006; 114[suppl I]:I-33-I-36.

Leon Axel, et al., "MR Imaging of Motion with Spatial Modulation of Magnetization", Radiology, vol. 171, No. 3, pp. 841-845, Jun. 1989.

Leon Axel, et al., "Heart Wall Motion: Improved Method of Spatial Modulation of Magnetization for MR Imaging", Radiology, vol. 172, pp. 349-350, Aug. 1989.

Jaco J. M. Zwanenburg, et al., "Steady-State Free Precession With Myocardial Tagging: CSPAMM in a Single Breathhold", magnetic Resonance in Medicine 49:000-000, 2003.

Marco J. W. Gotte, et al., "Myocardial Strain and Torsion Quantified by Cardiovascular Magnetic Resonance Tissue Tagging Studies in Normal and Impaired Left Ventricular Function", Journal of the American College of Cardiology, vol. 48, Issue 10, Nov. 21, 2006, pp. 2002-2011.

K. Z. Adb-Elmoniem, et al., "Multi-slice three-dimensional myocardial strain tensor quantification using zHARP", Inf Process Med Imaging, 2007;20:62-73.

Susan L. Herz, et al., "Parameterization of Left Ventricular Wall Motion for Detection of regional Ischemia", Annals of Biomedical Engineering, vol. 33, No. 7, Jul. 2005, pp. 912-919.

PCT/US1009/030429 International Search Report; 4 pages.

Cupps Brian P et al: Myocardial Viability Mapping by Magnetic Resonance-Based Multiparametric Systolic Strain Analysis; Annals of Thoracic Surgery, NY NY; vol. 86, No. 5; Oct. 17, 2008; pp. 1546-1553.

Park J et al:Strain Analysis and Visualization: Left Ventricle of a Heart; Computers and Graphics, Elseiver, GB; vol. 24, No. 5; Oct. 1, 2000; pp. 701-714.

Jegathese C R et al: Cyber Heart: The Employment of an Iterative Design Process to Develop a Left Ventricular Heart Graphical Display; Cyberworlds, 2003, Proceedings, 2003 International Conference on Dec. 3-5, 2003, Piscataway JN, Dec. 3, 2003; pp. 237-244.

Garot J et al: Fast Determination of Regional Myocardial Strain Fields From Tagged Cardiac Images Using Harmonic Phase MRI; Circulation, vol. 101, 2000; pp. 981-988.

Oznur I et al; Strain Rates in the Normal and Ischemic Human Heart With MRI Tagging; Proceedings of the International Society for Magnetic Resonance in Medicine, 6th Scientific Meeting and Exhibition, Sydney Australia, Apr. 18-24, 1998; p. 870.

D'Hooge JE et al: Deformation Imaging by Ultrasound for the Assessment of Regional Myocardial Function; 2003 IEEE Ultrasonics Symposium Proceedings; Honolulu Oct. 5, 2003; NY NY; IEEE vol. 1, pp. 3-12.

Alejandro F Frangi et al: Three-Dimensional Modeling for Functional Analysis of Cardiac Images: A Review; IEEE Transactions on Medical Imaging, IEEE Service Center, Piscataway NJ; vol. 20, No. 1, Jan. 1, 2001.

Cupps B P et al: Principal Strain Orientation in the Normal Human Left Ventricle; The Annals of Thoracic Surgery, Elsevier, vol. 79, No. 4, Apr. 1, 2005; pp. 1338-1343.

* cited by examiner

METHOD FOR QUANTITATIVELY MAPPING MYOCARDIAL CONTRACTILE FUNCTION WITH MAGNETIC RESONANCE BASED MULTIPARAMETRIC STRAIN ANALYSIS

CROSS-REFERENCE TO RELATED APPLICATIONS

This application claims the benefit of U.S. Provisional patent application Ser. No. 61/020,068 filed on Jan. 9, 2008 and entitled "Method and System For Analyzing Cardiac Function", Ser. No. 61/020,060 filed on Jan. 9, 2008 and entitled "Method and System for Displaying Cardiac Function", and Ser. No. 61/092,999 filed on Aug. 29, 2008 and entitled "Method for Quantitatively Mapping Myocardial Contractibility With Magnetic Resonance Based Multiparametric Strain Analysis."

STATEMENT REGARDING FEDERALLY SPONSORED RESEARCH

This invention was made with United States government support awarded by the following agency: NIH HL069967 and NIH HL064869. The United States has certain rights in this invention.

BACKGROUND OF THE INVENTION

The field of the invention is magnetic resonance imaging (MRI) systems and methods. More particularly, the invention relates to the quantitative assessment of regional myocardial contractile function by producing strain maps from acquired MRI data.

When a substance such as human tissue is subjected to a uniform magnetic field (polarizing field $B_0$), the individual magnetic moments of the excited nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped", into the x-y plane to produce a net transverse magnetic moment $M_t$. A signal is emitted by the excited nuclei or "spins", after the excitation signal $B_1$ is terminated, and this signal may be received and processed to form an image.

When utilizing these "MR" signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

The measurement cycle used to acquire each MR signal is performed under the direction of a pulse sequence produced by a pulse sequencer. Clinically available MRI systems store a library of such pulse sequences that can be prescribed to meet the needs of many different clinical applications. Research MRI systems include a library of clinically proven pulse sequences and they also enable the development of new pulse sequences.

The MR signals acquired with an MRI system are signal samples of the subject of the examination in Fourier space, or what is often referred to in the art as "k-space". Each MR measurement cycle, or pulse sequence, typically samples a portion of k-space along a sampling trajectory characteristic of that pulse sequence. Most pulse sequences sample k-space in a roster scan-like pattern sometimes referred to as a "spin-warp", a "Fourier", a "rectilinear" or a "Cartesian" scan. The spin-warp scan technique is discussed in an article entitled "Spin-Warp MR Imaging and Applications to Human Whole-Body Imaging" by W. A. Edelstein et al., Physics in Medicine and Biology, Vol. 25, pp. 751-756 (1980). It employs a variable amplitude phase encoding magnetic field gradient pulse prior to the acquisition of MR spin-echo signals to phase encode spatial information in the direction of this gradient. In a two-dimensional implementation (2DFT), for example, spatial information is encoded in one direction by applying a phase encoding gradient (Gy) along that direction, and then a spin-echo signal is acquired in the presence of a readout magnetic field gradient ($G_x$) in a direction orthogonal to the phase encoding direction. The readout gradient present during the spin-echo acquisition encodes spatial information in the orthogonal direction. In a typical 2DFT pulse sequence, the magnitude of the phase encoding gradient pulse $G_y$ is incremented ($\Delta G_y$) in the sequence of measurement cycles, or "views" that are acquired during the scan to produce a set of k-space MR data from which an entire image can be reconstructed.

There are many other k-space sampling patterns used by MRI systems These include "radial", or "projection reconstruction" scans in which k-space is sampled as a set of radial sampling trajectories extending from the center of k-space as described, for example, in U.S. Pat. No. 6,954,067. The pulse sequences for a radial scan are characterized by the lack of a phase encoding gradient and the presence of a readout gradient that changes direction from one pulse sequence view to the next. There are also many k-space sampling methods that are closely related to the radial scan and that sample along a curved k-space sampling trajectory rather than the straight line radial trajectory. Such pulse sequences are described, for example, in "Fast Three Dimensional Sodium Imaging", MRM, 37:706-715, 1997 by F. E. Boada, et al. and in "Rapid 3D PC-MRA Using Spiral Projection Imaging", Proc. Intl. Soc. Magn. Reson. Med. 13 (2005) by K. V. Koladia et al and "Spiral Projection Imaging: a new fast 3D trajectory", Proc. Intl. Soc. Mag. Reson. Med. 13 (2005) by J. G. Pipe and Koladia.

An image is reconstructed from the acquired k-space data by transforming the k-space data set to an image space data set. There are many different methods for performing this task and the method used is often determined by the technique used to acquire the k-space data. With a Cartesian grid of k-space data that results from a 2D or 3D spin-warp acquisition, for example, the most common reconstruction method used is an inverse Fourier transformation ("2DFT" or "3DFT") along each of the 2 or 3 axes of the data set. With a radial k-space data set and its variations, the most common reconstruction method includes "regridding" the k-space samples to create a Cartesian grid of k-space samples and then perform a 2DFT or 3DFT on the regridded k-space data set. In the alternative, a radial k-space data set can also be transformed to Radon space by performing a 1 DFT of each radial projection view and then transforming the Radon space data set to image space by performing a filtered backprojection.

The ability to accurately quantify regional myocardial contractile function in the clinical setting has profound consequences in the clinical management of patients whose myocardial pathological processes demonstrate, and whose clinical course is dependent upon, regional and transmural variances in myocardial contractile function. Most notably, this impacts the clinical management of patients with ischemic cardiomyopathy secondary to atherosclerotic coronary artery disease. The most common clinical manifestation of this disease process is intermittent or permanent impairment of myocardial contractile function in the regions of the left ventricle whose coronary arterial blood supply is directly compromised by atherosclerotic occlusive disease. It is well established that the degree of impairment, the quantity of myocardium that is impaired, and the reversibility of the impairment all have a direct influence on clinically observed morbidity and mortality. In addition to ischemic cardiomyopathy, the quantification of regional myocardial contractile function is also an important tool in the clinical assessment of disease processes once felt to be regionally homogeneous, such as cardiomyopathy secondary to valvular or idiopathic myopathic processes.

In general, a more accurate characterization of regional and transmural contractile function impacts the investigation of human pathophysiological processes that directly affect the myocardium, such as the cardiomyopathies that accompany valvular, coronary arterial, and primary myocardial diseases. For example, the uniform nature of the circumferential myocardial thinning and symmetrical short axis cross-sectional shape that characterizes the left ventricular geometry of patients with non-ischemic, non-valvular dilated cardiomyopathy has long suggested a homogeneous myocardial process of injury. It is now recognized, however, that the pathological influence of secondary remodeling on both adjacent and distant non-injured myocardium can render uniform and homogeneous global ventricular geometrical changes from a heterogeneous injury process. In fact, previous investigations have suggested heterogeneous contractile changes in patients having non-ischemic, non-valvular dilated cardiomyopathy.

Catheter-based or cardiac surgical coronary revascularization procedures are the most commonly applied therapeutic interventions in patients with ischemic cardiomyopathy. Although many clinical factors are important in directing these high-risk interventions, the presence of viable myocardium in the distribution of target atherosclerotic vessels remains the primary factor in determining if intervention is warranted. Revascularizing viable myocardium improves outcomes; however, high-risk revascularization procedures directed at nonviable myocardium do not improve outcomes over medical therapy alone. Improving the accuracy of the detection and full characterization of the viable myocardium is, therefore, a critical factor in improving the outcomes in this high-risk patient population.

Currently utilized viability testing methodologies, such as thallium single-photon emission computed tomography (SPECT) imaging, positron emission tomography (PET) imaging, delayed-enhancement magnetic resonance imaging (MRI), and dobutamine echocardiography are effective in directing clinical decision-making. However, these imaging modalities are limited in the accuracy of their regional and transmural characterization of myocardial viability as a result of the qualitative nature of the images they produce. This qualitative image output predisposes to variability in the interpretation made by clinicians of regional involvement in irreversible ischemic injury. For example, multiple clinicians may variably characterize an area of nonviable myocardium that resulted from left anterior descending coronary artery occlusion and which overlaps anterior, anterolateral, and anteroseptal regions, as well as extending a variable distance from base to apex in each of these left ventricular (LV) regions.

In a similar fashion, quantification of the degree of transmural injury is also limited with current modalities. Myocardial ischemia resulting from coronary artery occlusive disease is well known to affect the myocardium in a non-uniform transmural distribution, with the subendocardium being more susceptible to ischemia than the epicardial myocardium. The ability to accurately differentiate isolated subendocardial infarction from transmural injury has important clinical implications in regard to prognosis, as well as the appropriate application of therapeutic intervention methods. Thallium SPECT imaging, PET imaging, delayed-enhancement MRI, and dobutamine echocardiography only offer a qualitative characterization of transmural inhomogeneity. Once again, a lack of quantification of transmural viability predisposes to inconsistency in clinician interpretation.

Magnetic resonance imaging has excellent spatial and temporal resolution and has the unique ability to track the systolic deformation of gridlines laid down by the radiofrequency tagging of myocardial tissue. For example, a pulse sequence such as the one described in U.S. Pat. Nos. 5,054,489; 5,217,016; 5,275,163; 6,171,241 and 6,721,589 can be utilized to produce a grid of dark lines on an MR image acquired at a reference cardiac phase and the deformation of these grid lines can be monitored in MR images acquired at other cardiac phases to determine the deformation of the patient's heart wall during a heart beat. This information, combined with excellent tissue boundary resolution without the need for intravenous contrast agents and the absence of radiation exposure, make MRI highly attractive as a clinically applicable imaging modality to assess regional differences in myocardial contractile function.

Many different MRI methods have been proposed to characterize left ventricle contractile function. These include methods disclosed in U.S. Pat. Nos. 6,757,423 and 7,030,874, as well as pending U.S. Patent Applications US2002/0176637 and US2008/0077032. These methods purport to calculate strain, torsion and other mechanical properties of myocardial function, but none disclose the calculation of a multiparameter strain index that correlates with abnormal contractile function.

SUMMARY OF THE INVENTION

The present invention overcomes the aforementioned drawbacks by providing a method for accurately quantifying regional myocardial contractile function. More specifically, a method for multiparametric strain analysis is employed to provide accurate quantification of regional myocardial contractile function in a clinical setting.

One aspect of the present invention is to provide a method for quantifying regional differences in contractile function from three-dimensional left ventricular systolic strain maps that are generated from intra-myocardial point displacement information. This information is acquired by MRI-based systolic tracking of radiofrequency (RF) tissue-tagging gridlines. The capabilities of this method make it well suited for regional quantification of contractile function in patients with primary cardiac muscular disease (i.e., dilated cardiomyopathy), coronary artery disease and regional myocardial dysfunction (i.e., ischemic cardiomyopathy), or myocardial dysfunction secondary to valvular disease (i.e., valvular cardiomyopathy). The displacement of the tag lines, which are produced during the MRI acquisition, is monitored to determine systolic tag surface deformation. In turn, this deformation is utilized to generate highly accurate, left ventricular (LV) systolic strain maps. A fitting of displacement data measured from the systolic deformation of the tag surfaces provides a continuous description of displacement throughout a heart model. Utilizing the results of this fitting, strain is computed at a plurality of points in the heart model, that are isotropically distributed throughout the heart model.

Multiple strain indices are computed using this method and three of these indices (circumferential strain, longitudinal strain, and the minimum principal strain angle) demonstrate accurate characterization of regional and transmural myocardial function.

It is another aspect of the present invention to provide a method for quantitative parametric systolic strain analysis. The strain indices computed at each point on the heart model are "normalized" by comparing them with the strain reference values at corresponding points on a reference heart model. This reference heart model includes the normal average strain and the normal standard strain deviation for all the strain parameters at each of the points in the "normal" human left ventricle. This reference heart model may be produced from data acquired from many healthy individuals or it may be produced from data previously acquired from the same subject. The resulting normalized strain indices relate the patient-specific strain measurements to the average strain value and standard deviation in the reference heart model. This enables different patient-specific parameters with widely variable normal ranges to be combined and parameterized in terms of amount of deviation from the reference model.

The present invention allows the characterization of patient-specific strain measurements to normal strain values in the same way that many routine laboratory blood values are related to the expected norm by comparison to the normal average and standard deviation ranges. For example, a normal reference population may have an average serum K+ level of 4.0 with the lower limit of normal being 3.5 and the upper limit of normal being 5.5. This serum K+ "normal" range is determined by two standard deviations from the normal average. With the assumption of a normal distribution of data, this would mean that the patient and their physician can know that 95% of normal subject serum K+ levels fall within this range and that if the patient's serum K+ falls outside of this range it is most likely abnormal. The present invention enables similar assumptions to be made in regard to the patient's left ventricular regional myocardial contractile function.

Another aspect of the present invention is to provide a multiparametric strain index that is particularly useful in analyzing myocardial function. This multiparametric strain index is produced at points in the heart by combining separate normalized strain indices at each point. The combination is a weighted sum of the normalized strain indices. The strain index is a complex mathematical description of three-dimensional myocardial contraction that may be postprocessed in decision-making algorithms or stored in electronic medical records. The multiparametric strain index may also be used to produce a parametric image of the heart in which the multiparametric strain index values modulate pixel color in an anatomic image of the heart or a heart model image.

The present invention enables a more accurate detection of abnormal contractile patterns associated with injured, ischemic, or nonviable myocardium. MRI tagging methods are limited in the number of tag lines that can fit transmurally and hence contribute to the density of measured displacement information in the radial direction. As a result, radial strain measurements are inconsistent. Longitudinal, circumferential and minimum principal strain directions can be consistently measured using MRI tagging methods, however, and the multiparametric strain index produced from these measurements yields an accurate measurement of abnormal contractile patterns. One of the advantages of the multiparametric strain index according to the present invention is the ability to exclude or downplay the significance of those strain parameters that are less accurate in favor of those that are more accurately measured or more clinically relevant by appropriately weighting them.

The present invention also enables changes in the subject's heart function to be measured over time. Sets of multiparametric strain indices may be acquired over a period of time and a parametric image of the subject's heart may be produced which results from the subtraction of the later image from the earlier image thus demonstrating the changes that have occurred in the strain indices over time. Also, a whole heart or whole regional composite score can be calculated by averaging the multiparametric strain indices in each set and the composite scores may be compared to indicate change in overall cardiac function.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE PREFERRED EMBODIMENT

Figure 1:
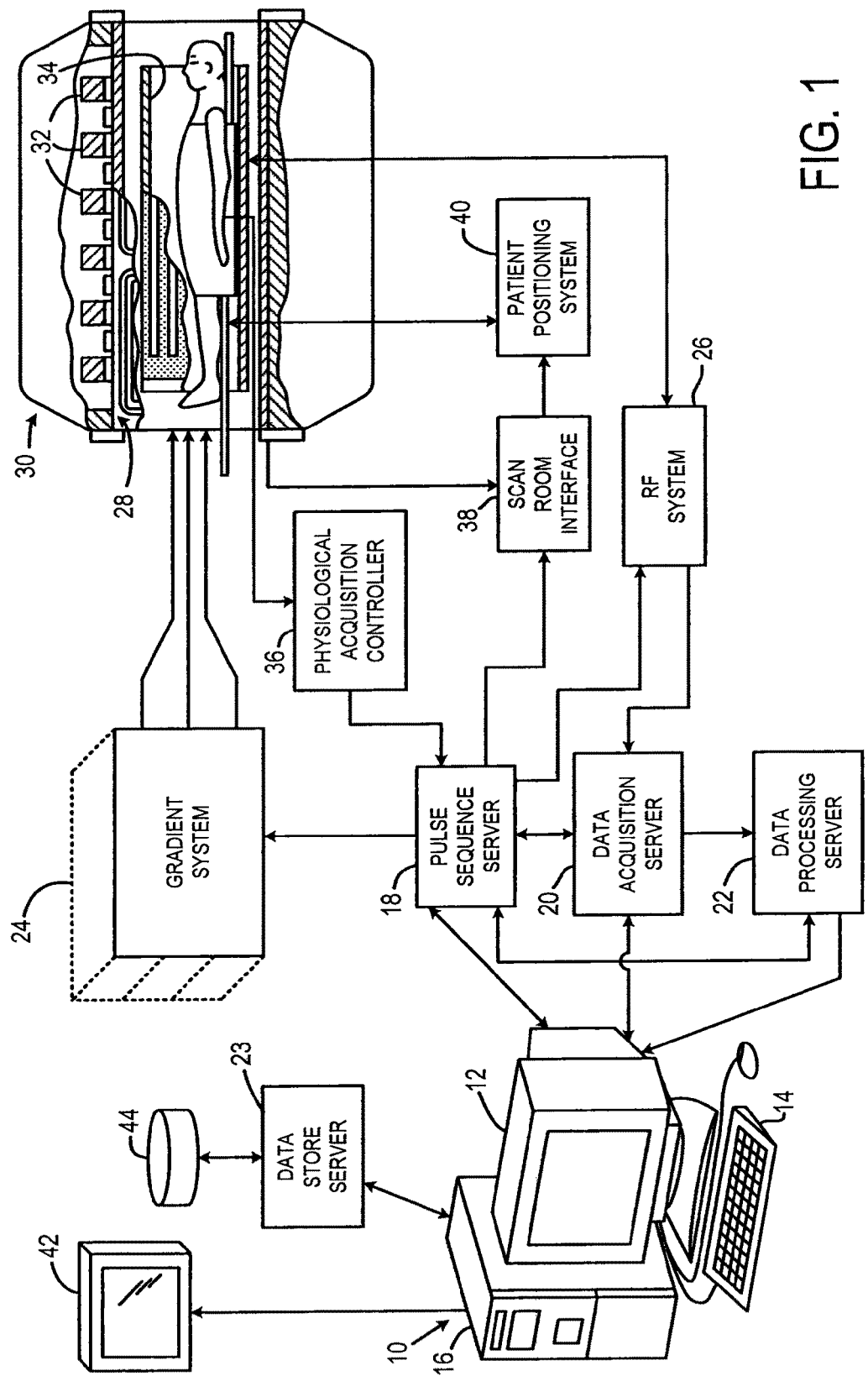
FIG. 1 is a block diagram of an MRI system that employs the present invention.

Referring particularly to FIG. 1, the preferred embodiment of the invention is employed in an MRI system. The MRI system includes a workstation 10 having a display 12 and a keyboard 14. The workstation 10 includes a processor 16 that is a commercially available programmable machine running a commercially available operating system. The workstation 10 provides the operator interface that enables scan prescriptions to be entered into the MRI system. The workstation 10 is coupled to four servers: a pulse sequence server 18; a data acquisition server 20; a data processing server 22, and a data store server 23. The workstation 10 and each server 18, 20, 22 and 23 are connected to communicate with each other.

The pulse sequence server 18 functions in response to instructions downloaded from the workstation 10 to operate a gradient system 24 and an RF system 26. Gradient waveforms necessary to perform the prescribed scan are produced and applied to the gradient system 24 that excites gradient coils in an assembly 28 to produce the magnetic field gradients $G_x$, $G_y$ and $G_z$ used for position encoding MR signals. The gradient coil assembly 28 forms part of a magnet assembly 30 that includes a polarizing magnet 32 and a whole-body RF coil 34.

RF excitation waveforms are applied to the RF coil 34 by the RF system 26 to perform the prescribed magnetic resonance pulse sequence. Responsive MR signals detected by the RF coil 34 or a separate local coil (not shown in FIG. 1) are received by the RF system 26, amplified, demodulated, filtered and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform. The generated RF pulses may be applied to the whole body RF coil 34 or to one or more local coils or coil arrays (not shown in FIG. 1).

The RF system 26 also includes one or more RF receiver channels. Each RF receiver channel includes an RF amplifier that amplifies the MR signal received by the coil to which it is connected and a detector that detects and digitizes the I and Q quadrature components of the received MR signal. The magnitude of the received MR signal may thus be determined at any sampled point by the square root of the sum of the squares of the I and Q components:

$$M = \sqrt{I^2 + Q^2},$$

and the phase of the received MR signal may also be determined:

$$\phi = \tan^{-1}\left(\frac{Q}{I}\right).$$

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 that receives signals from various sensors associated with the condition of the patient and the magnet system. It is also through the scan room interface circuit 38 that a patient positioning system 40 receives commands to move the patient to desired positions during the scan.

The digitized MR signal samples produced by the RF system 26 are received by the data acquisition server 20. The data acquisition server 20 operates in response to instructions downloaded from the workstation 10 to receive the real-time MR data and provide buffer storage such that no data is lost by data overrun. In some scans the data acquisition server 20 does little more than pass the acquired MR data to the data processor server 22. However, in scans that require information derived from acquired MR data to control the further performance of the scan, the data acquisition server 20 is programmed to produce such information and convey it to the pulse sequence server 18. For example, during prescans MR data is acquired and used to calibrate the pulse sequence performed by the pulse sequence server 18. Also, navigator signals may be acquired during a scan and used to adjust RF or gradient system operating parameters or to control the view order in which k-space is sampled. And, the data acquisition server 20 may be employed to process MR signals used to detect the arrival of contrast agent in an MRA scan. In all these examples the data acquisition server 20 acquires MR data and processes it in real-time to produce information that is used to control the scan.

The data processing server 22 receives MR data from the data acquisition server 20 and processes it in accordance with instructions downloaded from the workstation 10. Such processing may include, for example: Fourier transformation of raw k-space MR data to produce two or three-dimensional images; the application of filters to a reconstructed image; the performance of a backprojection image reconstruction of acquired MR data; the calculation of functional MR images; the calculation of motion or flow images, etc.

Images reconstructed by the data processing server 22 are conveyed back to the workstation 10 where they are stored. Real-time images are stored in a data base memory cache (not shown) from which they may be output to operator display 12 or a display 42 that is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

Figure 2:
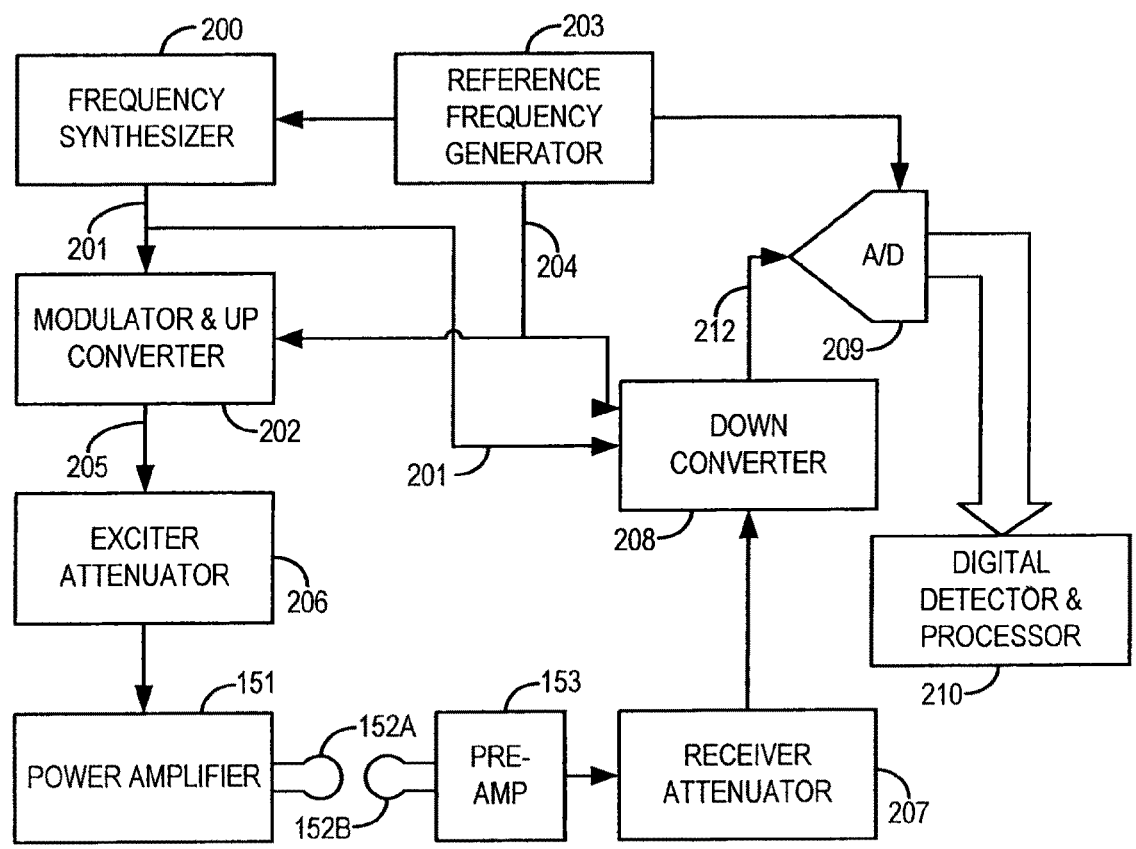
FIG. 2 is a block diagram of an RF system that forms part of the MRI system of FIG. 1.

As shown in FIG. 1, the RF system 26 may be connected to the whole body RF coil 34, or as shown in FIG. 2, a transmitter section of the RF system 26 may connect to one RF coil 152A and its receiver section may connect to a separate RF receive coil 152B. Often, the transmitter section is connected to the whole body RF coil 34 and each receiver section is connected to a separate local coil 152B.

Referring particularly to FIG. 2, the RF system 26 includes a transmitter that produces a prescribed RF excitation field. The base, or carrier, frequency of this RF excitation field is produced under control of a frequency synthesizer 200 that receives a set of digital signals from the pulse sequence server 18. These digital signals indicate the frequency and phase of the RF carrier signal produced at an output 201. The RF carrier is applied to a modulator and up converter 202 where its amplitude is modulated in response to a signal R(t) also received from the pulse sequence server 18. The signal R(t) defines the envelope of the RF excitation pulse to be produced and is produced by sequentially reading out a series of stored digital values. These stored digital values may, be changed to enable any desired RF pulse envelope to be produced.

The magnitude of the RF excitation pulse produced at output 205 is attenuated by an exciter attenuator circuit 206 that receives a digital command from the pulse sequence server 18. The attenuated RF excitation pulses are applied to the power amplifier 151 that drives the RF coil 152A.

Referring still to FIG. 2 the signal produced by the subject is picked up by the receiver coil 152B and applied through a preamplifier 153 to the input of a receiver attenuator 207. The receiver attenuator 207 further amplifies the signal by an amount determined by a digital attenuation signal received from the pulse sequence server 18. The received signal is at or around the Larmor frequency, and this high frequency signal is down converted in a two step process by a down converter 208 that first mixes the MR signal with the carrier signal on line 201 and then mixes the resulting difference signal with a reference signal on line 204. The down converted MR signal is applied to the input of an analog-to-digital (A/D) converter 209 that samples and digitizes the analog signal and applies it to a digital detector and signal processor 210 that produces 16-bit in-phase (I) values and 16-bit quadrature (Q) values corresponding to the received signal. The resulting stream of digitized I and Q values of the received signal are output to the data acquisition server 20. The reference signal as well as the sampling signal applied to the A/D converter 209 are produced by a reference frequency generator 203.

The preferred embodiment of the invention includes: a data acquisition phase in which MR data is acquired from the subject of the scan using the MRI system of FIG. 1; an image reconstruction phase in which images are produced from the acquired MR data; and then a post processing phase in which the reconstructed images are used along with a previously produced reference heart model to produce a multiparametric strain index map. The latter two phases may be performed on the MRI system of FIG. 1 although the acquired MR data or reconstructed images may also be off-loaded and processed on a workstation or the like as described below.

Figure 3:
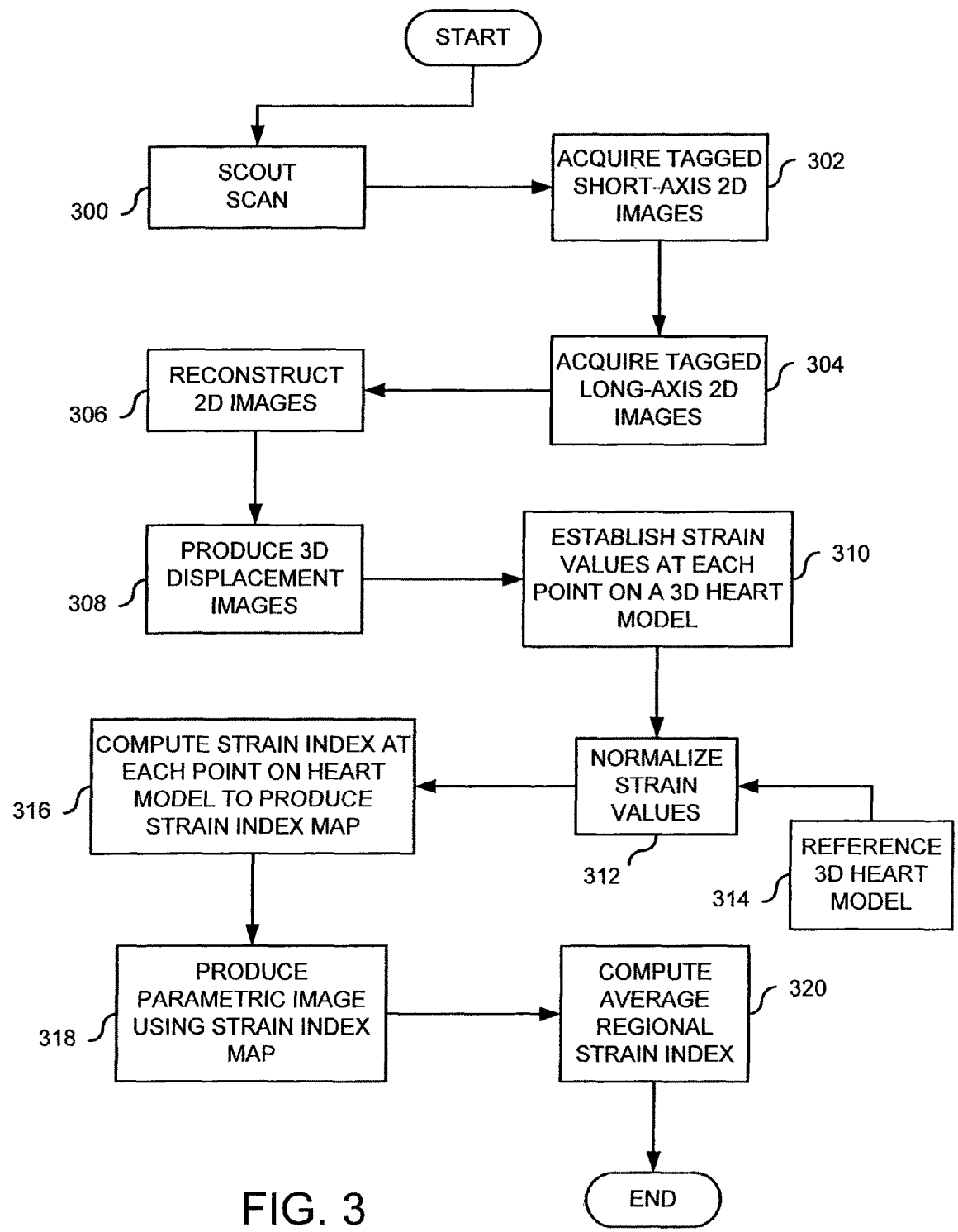
FIG. 3 is a flowchart of the steps used to perform the preferred embodiment of the invention.

Referring particularly to FIG. 3, the first step as indicated at process block 300 is to place the subject in the MRI system and perform a scout scan using an imaging pulse sequence such as a balanced SSFP. An image of the subject's heart is produced which enables the location and orientation of the heart to be determined. This enables the long axis of the left ventricle to be located so that the image acquisition phase to follow can be accurately prescribed. It also enables a quality anatomical image of the heart to be produced, which enables tissue boundaries to be located, and which provides the anatomical information in a final parametric image that may be produced as described below.

The image acquisition phase includes the acquisition of tagged short-axis 2D images as indicated at process block 302 and the acquisition of tagged long-axis 2D images as indicated at process block 304. The short-axis images are acquired in parallel planes, for example at 8 mm intervals, beginning at the level of the mitral valve and extending downward therefrom to an imaging plane that includes substantially only the apical myocardium. Four long-axis images passing through the centroid of the left ventricle are also acquired. Each long-axis image extends radically outward from the centroid and these four 2D images are equally spaced at 45 degrees with respect to each other.

Figure 4:
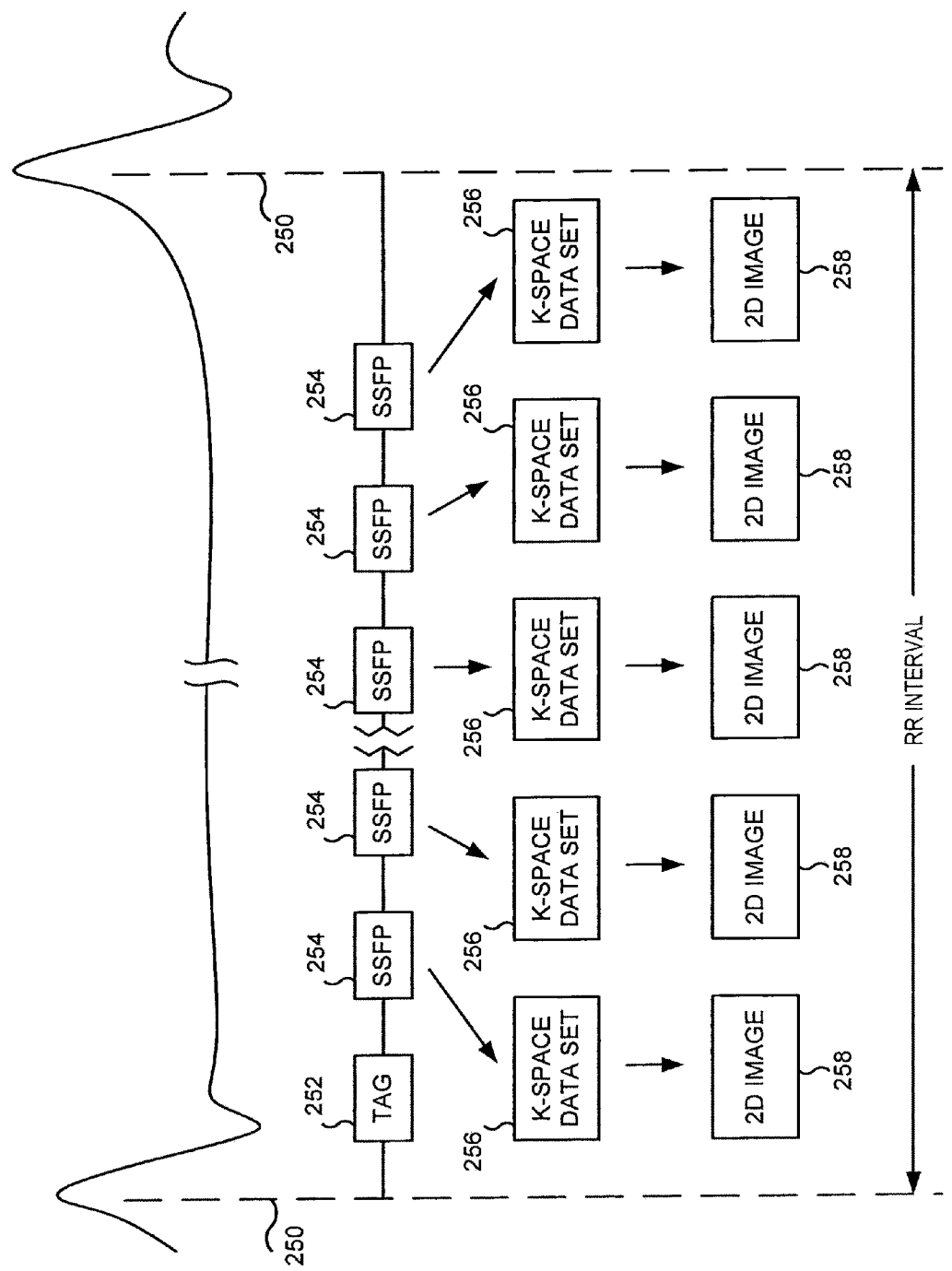
FIG. 4 is a graphic representation of the MR data acquisition method used with the MRI system of FIG. 1.
Figure 5:
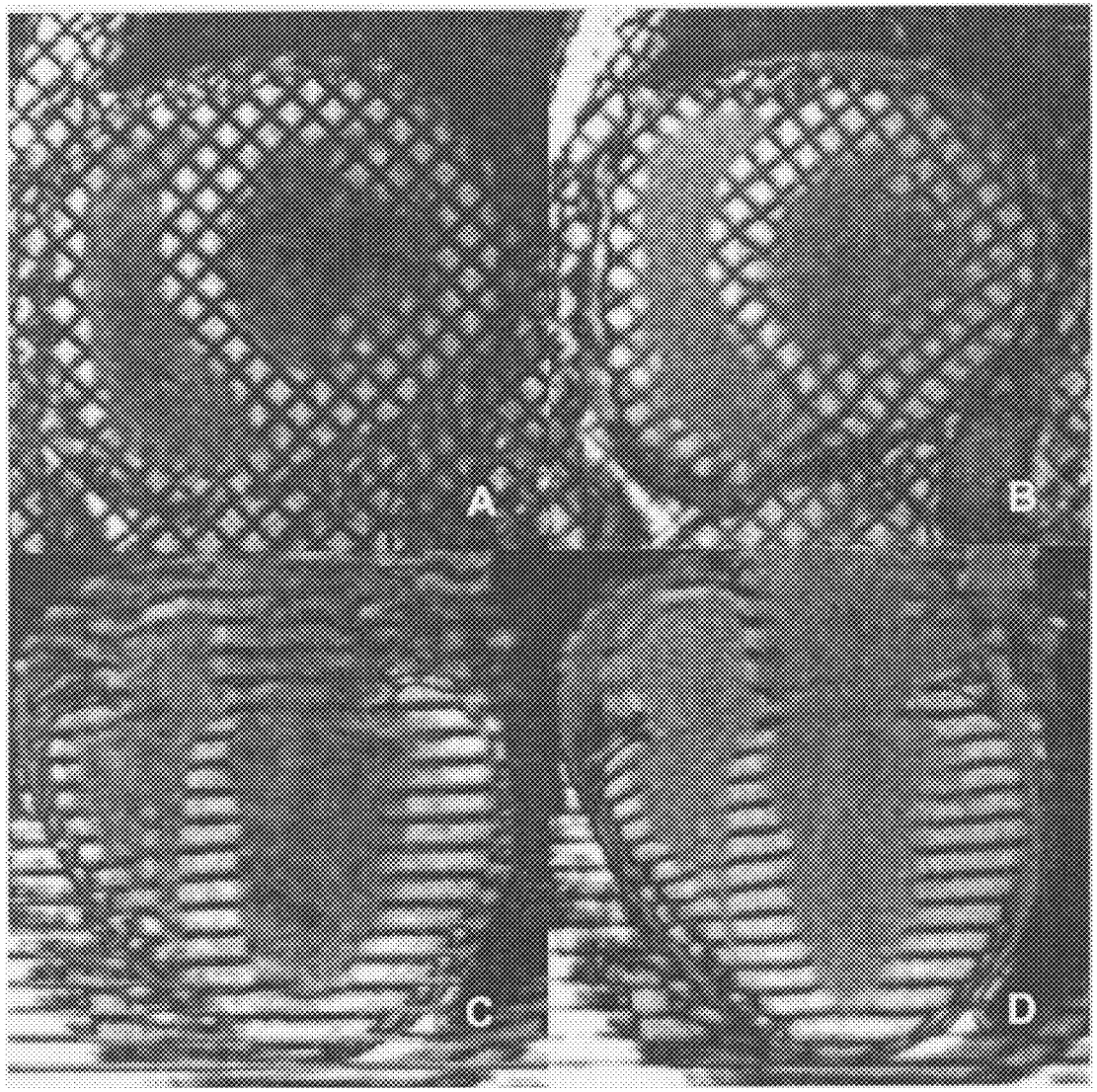
FIG. 5 is an exemplary tagged image acquired with the data acquisition of FIG. 4.

All of the tagged 2D images are acquired in the same manner. Referring to FIG. 4, the data acquisition sequence is initiated during each cardiac cycle by the ECG-R wave indicated at 250. At a predetermined cardiac phase after the R-wave trigger signal, a tag pulse sequence 252 is performed to properly prepare the spin magnetization. The tag pulse sequence includes a spatial modulation of magnetization (SPAMM) radiofrequency tissue-tagging preparation as described, for example, in the above-cited SPAMM patents and by L. Axel and L. Dougherty in "MR Imaging of motion with spacial modulation of magnetization", Radiology 1989; 171:841-845; and in "Heart Wall Motion: improved method of spatial modulation of magnetization for MR imaging", Radiology 1989; 172:349-350. Tag spacing is 8 mm in the preferred embodiment. The tagging sequence produces a grid of saturation slices throughout the subject's left ventricle at the preselected cardiac phase. The subsequent acquisition of MR images during systolic contraction enables one to track the radiofrequency tissue tag plane deformation during the heart beat and to apply mathematical modeling and advanced engineering analysis to the in vivo heart.

Referring still to FIG. 4, MR image data is acquired during each tagged cardiac cycle using two-dimensional balanced steady-state free precession (SSFP) pulse sequences. The SSFP acquisitions are arranged in segments 254 of pulse sequences acquired at substantially the same cardiac phase during a series of heart beats. Eleven different phase encodings are acquired during each segment and this enables a complete 2D k-space data set 256 to be acquired at each segment's cardiac phase in 20 to 25 heart beats. This in turn enables a 2D image 258 to be produced at each of a series of cardiac phases during systolic contraction. In the preferred embodiment the SSFP pulse sequence acquires a 2D slice having an 8 mm thickness and a field of view of 306×350 mm. The SSFP pulse sequence has a repetition time (TR) of 30.3 ms, an echo time (TE) of 2.2 ms and a k-space matrix of 168×256 points is sampled.

It should be apparent to those skilled in this art that many other MR data acquisition methods may be employed without departing from the present invention. Some of these variations are described by J. Zwanenberg et al. in "Steady-State Free Precission With Myocardial Tagging: CSPAMM in a Single Breathhold", Magnetic Resonance in Medicine 49:1-9 (2003). Other pulse sequences can be used to acquire the k-space MR data and techniques for reducing scan time, such as parallel imaging, may also be employed.

Referring again to FIG. 3, after the MR data acquisition phase is completed, the 2D k-space image data sets 256 are employed to reconstruct corresponding 2D images 258 as indicated at process block 306. This is accomplished with a two-dimensional, complex Fourier transformation of each acquired k-space data set. The signal magnitude is then calculated from the complex number at each image pixel.

Figure 6:
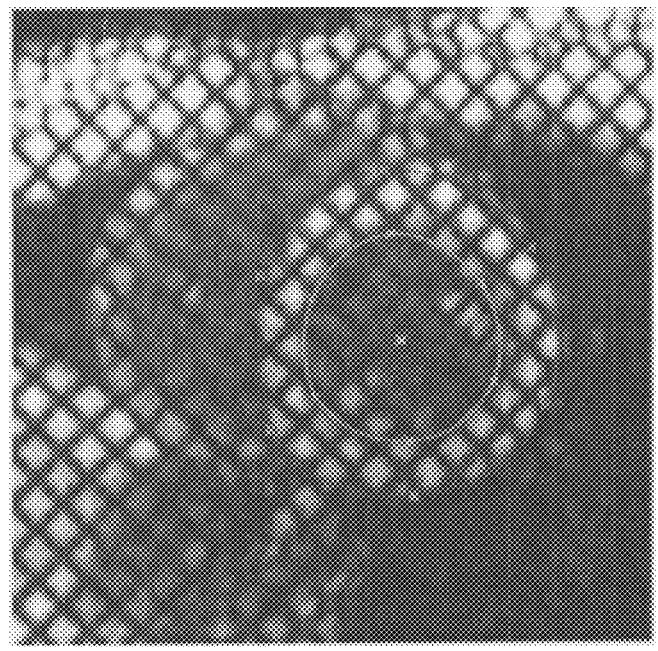
FIG. 6 is an exemplary tagged image showing the identification of a tissue boundary.

As indicated at process block 308, three-dimensional left ventricular strain images are produced from the intra-myocardial point displacement information embodied in the reconstructed tagged 2D images. Strain values are calculated using a method such as the one described, for example, by M. J. Moulton, et al., in "Spline Surface Interpolation for Calculating 3-D Ventricular Strains from MRI Tissue Tagging," Am. J. Physiol. 1996; 270(1 pt 2):H281-297. Ventricular wall boundaries, such as the endocardial and epicardial boundaries, are manually identified on the reconstructed short- and long-axis images as shown, for example, in FIG. 6. An initial spline curve approximation of the tag lines on the end diastolic images are produced based on the spacing between adjacent RF tags. The RF tags are subsequently tracked on images acquired at successive cardiac phases in a semi-automatic fashion using an iterative method that seeks to minimize image intensity along the spline curve. In this way, systolic displacements of the left ventricle are computed along the intersection curves of the short- and long-axis tag slices. The anterior and posterior junction points between the right ventricular free wall and septum on the most basal end diastolic short-axis image are used to create a series of, for example twelve, segment points on that image. These segment points serve as landmarks for creating the mesh for a finite element heart model used in the strain analysis.

Figure 7:
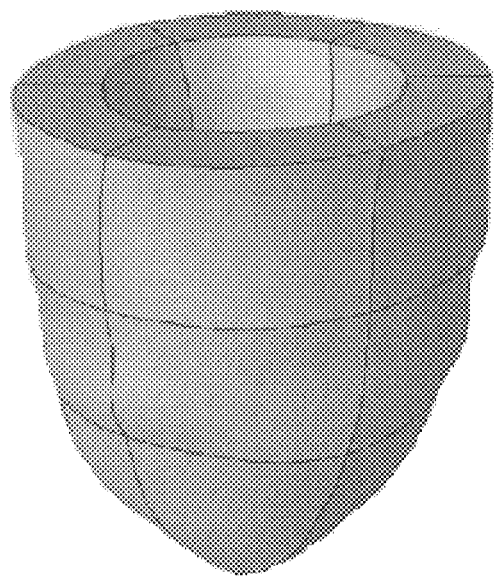
FIG. 7 is a schematic diagram of a region-based finite element model of the left ventricle.

For each segment point, a node is created at the base of the heart model by projecting the segment point to the bounding curves for the endocardial and epicardial surfaces. Additionally, a node is created at the apex of the epicardial surface. Additional nodes are created on the epicardial surface at equidistant points along surface curves joining each of the basal epicardial nodes with the node at the apex. The mesh for the heart model is completed by projecting the additional epicardial nodes to the endocardial surface. In the example mentioned above, in which twelve segment points are produced, the resultant heart model includes twelve hexahedral elements (anterior, anterolateral, posterolateral, posterior, posteroseptal and anteroseptal myocardial walls) at the base and mid-LV regions, and six pentahedral elements at the apex. An exemplary finite element LV heart model is shown in FIG. 7. This method of heart model construction allows for registration of different images of the left ventricle. The classification and nomenclature of the polyhedral elements follows the recommendations of the American Society of Echocardiography Committee on Standards as provided by R. M. Lang, et al., in "Recommendations for Chamber Quantification: A Report from the American Society of Echocardiography's Guidelines and Standards Committee and the Chamber Quantification Writing Group, Developed in Conjunction with the European Association of Echocardiography, a Branch of the European Society of Cardiology," J. Am. Soc. Echocardiogr. 2005; 18:1440-1463.

As indicated at process block 310, analysis of the displacement data is performed by employing a finite element analysis software package sold under the trade name "StressCheck" (ESRD, Inc., St. Louis, Mo.). A continuous representation of displacement over the domain of the heart model is obtained from a least squares fitting of the measured displacements utilizing the finite element basis functions. This fitting is done using the measurement analysis feature of the StressCheck program. Three strain measurements (circumferential strain, longitudinal strain and the principal strain angle) are computed on an evenly spaced grid in the element coordinate system (for example, at 15,300 points in the heart model).

3D images of the heart showing measured strain at various points thereon can be produced from the computed strain values. While this can provide some diagnostic information for the cardiologist, it is a teaching of the present invention that more diagnostic information can be produced if the measured strain values (x) at each point are compared with strain values at a corresponding point in a reference heart model. Human left ventricular strain is nonhomogeneous. As shown in FIG. 3 at process block 312, the measured strain values are compared to strain values at that corresponding anatomic point in a stored reference 3D heart model 314 in a process described in detail below and referred to herein as "normalization".

The stored reference 3D heart model 314 may be produced in a number of different ways. For example, the MR data used to produce it may be acquired from the current subject at an earlier stage of treatment. The MR data is acquired and processed as described above to produce reference strain values that are used in the normalization process to be described below to indicate changes that have occurred in the subject's heart. In the alternative, the reference 3D heart model 314 may be produced by scanning "normal" subjects and calculating the strain at each point in the 3D heart model. The mean strain value ($\mu$) is then calculated at each point in the 3D heart model from values at each corresponding point in the normal subjects, as well as the standard deviation ($\sigma$) of the normal strain values at each point. The reference 3D heart model thus stores the normal strain value ($\mu$) at each point in the 3D heart model as well as the normal standard deviation ($\sigma$).

The normalization process 312 calculates normalized strain values ($x_n$) at points on the 3D heart model. This normalized strain value, or z-score, is a numerical expression of the relationship of the measured subject-specific strain values to normal strain values. More specifically, the normalized strain $x_n$ is computed as the difference between the measured strain x and the normal mean strain value $\mu$ divided by the normal standard deviation $\sigma$ as follows:

$$x_n = (x-\mu)/\sigma \qquad (1)$$

While the normalized strain values can be used separately to provide improved diagnostic information, it is another discovery of the present invention that a single composite, multiparametric "strain index" value can be computed at each point on the 3D heart model by combining the three normalized strain values (i.e., circumferential, longitudinal, and principal strain angle) as indicated at process block 316. Multiple strain indices cannot be combined into a composite multiparametric strain index without normalization because the individual strain components have widely varying data ranges. The separate normalized strains can be combined in a number of ways, but the presently preferred method is simply to compute the average of the three or more than all three parametric values. It is contemplated that less than all three normalized strain values may be combined and that the combined parametric values may be weighted before being combined to form the single multiparametric strain index value.

The normalization of the measured patient-specific individual strain values allows the combination of multiple strain parameters, including their variable normal ranges, into a single multiparametric strain index. Therefore, the patient-specific multiparametric strain index for any one of the individual grid points throughout the left ventricle relates that patient's contractile function at that point in the myocardium to a normal and healthy individual.

As indicated at process block 318, the multiparametric strain index values may also be used to produce a parametric image. In one embodiment the multiparametric strain index values are used to modulate the color of pixels in a 3-D image of the heart model. The 15,300 multiparametric strain index values are arranged in tabular form and input into the StressCheck system, which performs a fitting of the data using its measurement analysis feature. A 3-D color contour model of the heart is output in which the multiparametric strain index value at locations therein is indicated by color. Example parametric images using this method are shown in FIGS. 7-10 described below.

The second embodiment produces a parametric image using an image of the subject's heart. This is accomplished by producing an anatomical image of the subject's heart using the MR image data acquired during the scout scan described above. Pixels in this image are color coded using the multiparametric strain index values at corresponding pixel locations. For example, locations where the subject's heart strain does not vary significantly from the reference heart model may be colored blue and locations of increasing variance may be color coded with successive colors of the spectrum.

As indicated at process block 320, it is also clinically useful to calculate an average multiparametric strain index for regions of the heart. This is done by averaging the multiparametric strain index values from the 15,300 left ventricular grid points that fall within a particular region of the heart. For example, the regions may be defined by the twelve hexahedral and six pentahedral regions described above and an average multiparametric strain index value may be calculated for each. This regional average multiparametric strain index value provides a number that is indicative of the contractile function in that region. This regional average multiparametric strain index may be compared to available clinical viability testing results to produce a characteristic curve and compute an optimized sensitivity and specificity for identifying non-viable regions of the subject's heart.

A composite score can also be computed which indicates the overall cardiac function. This composite score is calculated by averaging the multiparametric strain indices over a plurality of regions of the heart or over the entire heart. In the case of a whole left ventricular composite score that is obtained by averaging multiparametric strain indices, the number of standard deviations from the normal average relates to "normalcy" of the individual patient's global left ventricular contractile function in terms that are familiar to the medical community. For example, it is well understood that assuming a normal distribution of data, a composite score of 2.0 would indicate that the individual's left ventricular contractile function falls two standard deviations from the normal average and therefore there is a 95% chance that it is significantly abnormal. Composite scores produced from successive scans can be used to indicate changes in cardiac function over a period of time and provide an objective measure of treatment results or disease progression.

Figure 12:
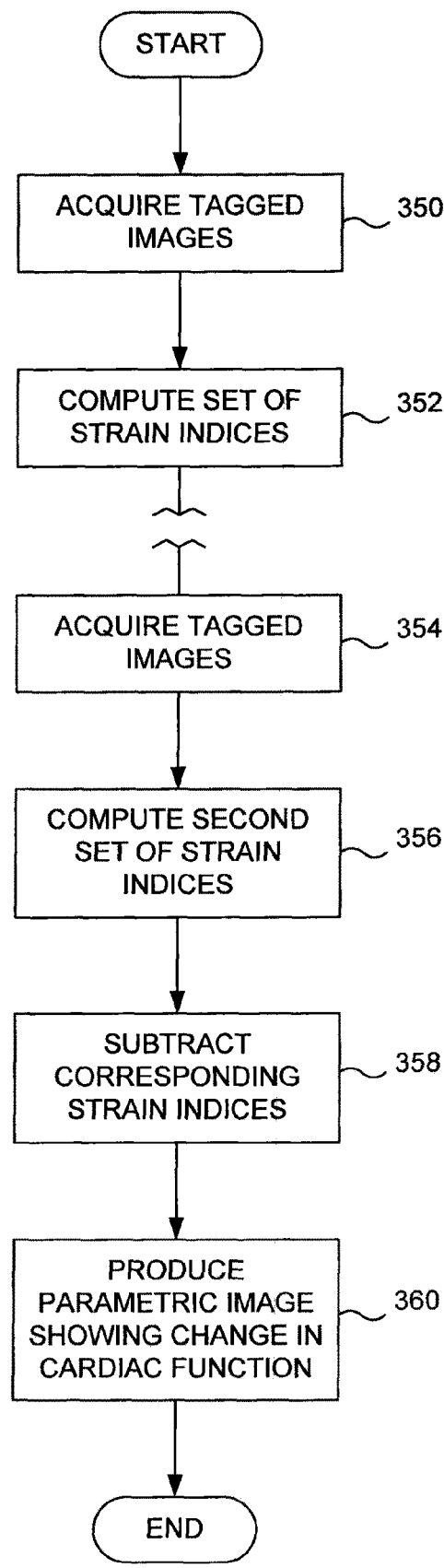
FIG. 12 is a flow chart of a method for measuring changes in cardiac function over time using the present invention.

Referring particularly to FIG. 12, the present invention may be employed to monitor in detail changes that occur in a subject's heart over a period of time. A sequence of two scans is depicted here, but it should be apparent that further scans can be conducted and processed as follows to continuously monitor the progression of heart disease and the effects of treatment.

As described above, tagged images are acquired during one scan, as indicated at process block 350 and a first set of strain indices are calculated from this data as indicated at process block 352. The scan may be repeated at a later date as indicated at process block 354 and a second set of strain indices is computed as indicated at process block 356. As indicated at process block 358, corresponding strain indices in the two sets are then subtracted to produce 15, 300 corresponding difference strain indices.

A parametric image is then produced as indicated at process block 360 using the set of difference strain indices. This color contour image therefore demonstrates the change that has occurred in terms of standard deviations from the normal average, which expresses the change in terms that are familiar to the medical clinician. As described above, this parametric image can be produced using the difference strain indices as input to the StressCheck program to produce a color coded image of the heart model. In the alternative, these difference strain indices may be used to modulate the color of pixels in an anatomical image of the subject's heart.

Figure 8:
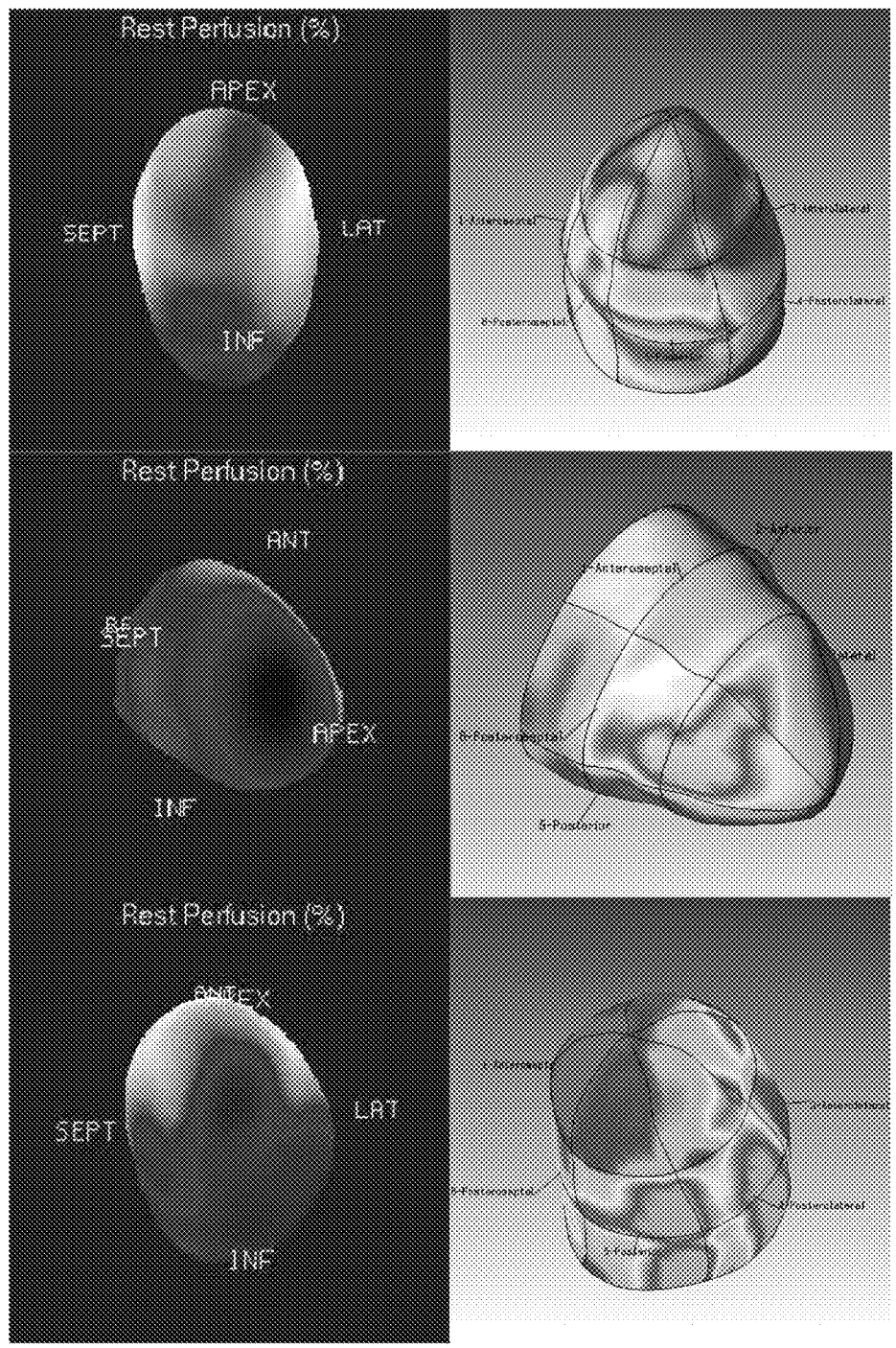
FIG. 8 is a series of SPECT images on the left compared with left ventricular multiparametric myocardial strain color-contour images produced in accordance with the present invention.

Referring particularly to FIG. 8, thallium single-positron emission computed tomography (SPECT) viability imaging versus magnetic resonance imaging (MRI)-based multiparametric strain index color-contour modeling is shown. Similarity is demonstrated between the blue areas of irreversible abnormal perfusion in the left-sided thallium SPECT image and the yellow (index=1.5) and red (index=2.25) areas of the corresponding MRI-based multiparametric strain index color-contour images on the right. For each of three representative patients, a thallium SPECT scan on the left is compared with its corresponding multiparametric strain index three-dimensional color-contour model on the right. Each three-dimensional multiparametric strain image is rotated to obtain the anatomically analogous view of the myocardial region of interest. The common finding of extension of infarction boundaries across multiple regions of the left ventricle is well demonstrated. In FIG. 8, the abbreviations ANT=anterior; INF=inferior; LAT=lateral; and SEPT=septal are used.

Figure 9:
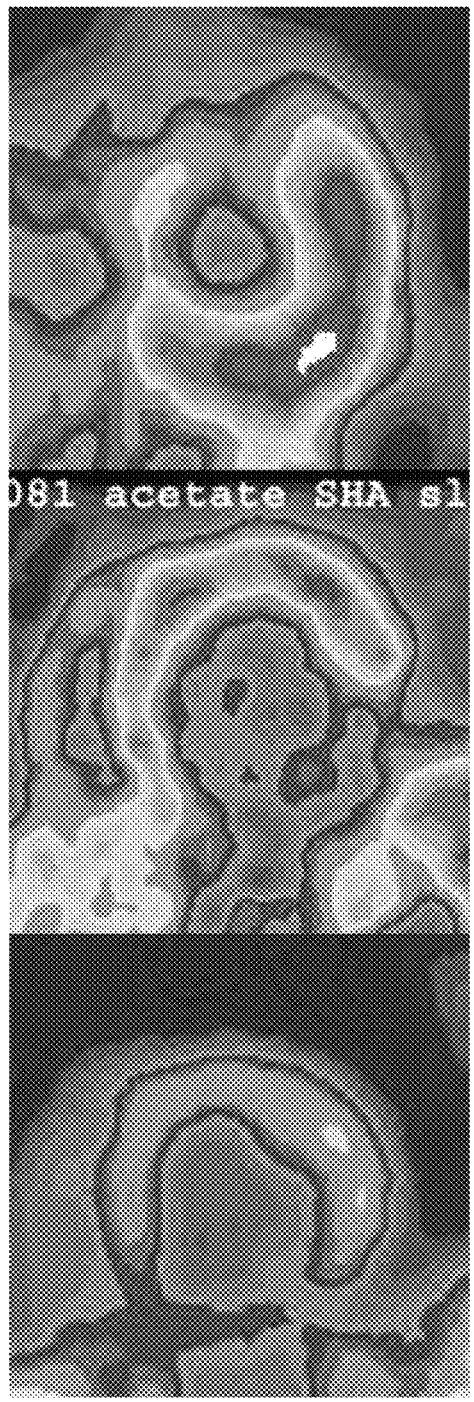
FIG. 9 is a series of PET images on the left compared with left ventricular multiparametric myocardial strain color-contour images produced in accordance with the present invention.
Figure 9:
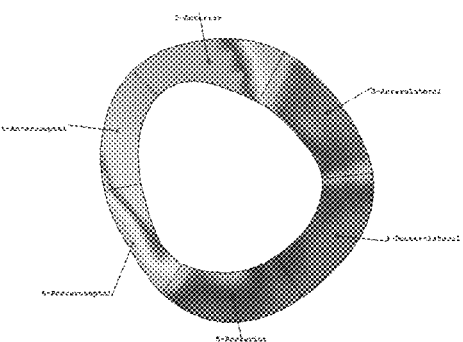
Figure 9:
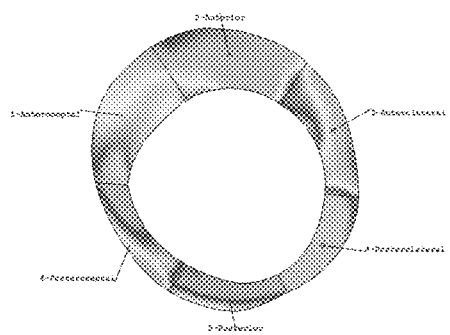
Figure 9:
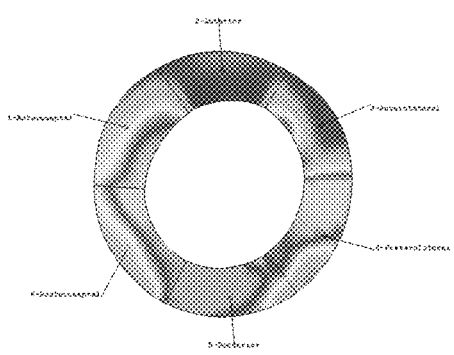

Referring particularly to FIG. 9, magnetic resonance imaging (MRI)-based multiparametric strain index color-contour modeling versus positron emission tomography (PET) viability imaging is shown. The PET scan results from 3 representative patients are presented in two-dimensional cross-sectional format. A corresponding two-dimensional slice is obtained for comparison by subjecting the MRI-based multiparametric strain index three-dimensional color-contour model to a post-processing cutting tool. In each comparison, the PET scan is found on the left with a comparable slice through the color-contour map in the same patient being found immediately to the right. Nonviable areas on the PET images are represented by a gap in the red, yellow, or green circular contour of the ventricular cross-section. Once again, similarities are demonstrated between the PET nonviable regions on the left and the yellow (index=1.5) and red (index=2.25) areas of the corresponding MRI-based multiparametric strain index color-contour images on the right. The propensity of irreversible injury from myocardial infarction to extend across multiple regional boundaries of the heart is again apparent.

Figure 10:
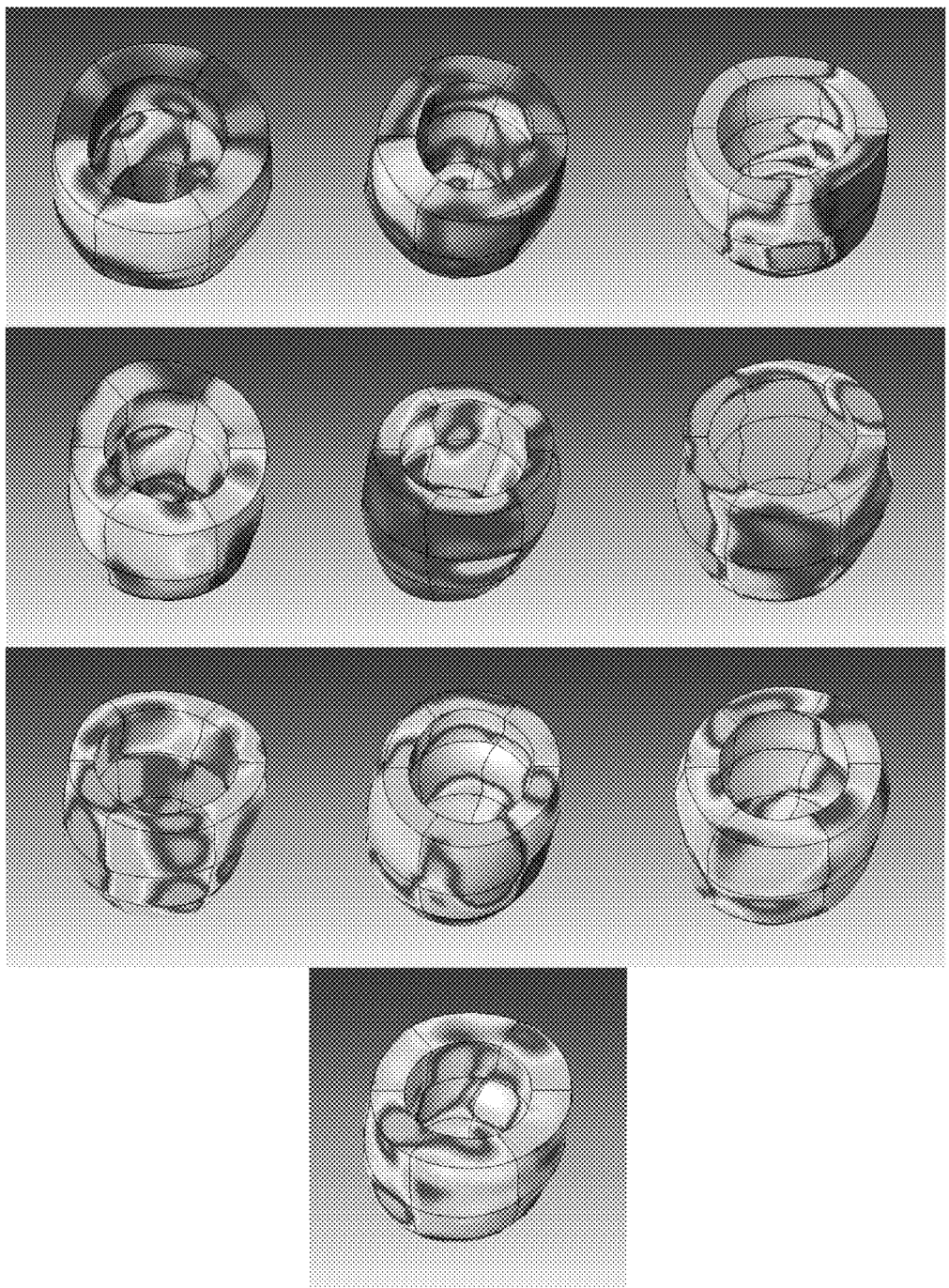
FIG. 10 is a series of left ventricular multiparametric myocardial strain color-contour images produced in accordance with the present invention.

Referring particularly to FIG. 10, MRI-based multiparametric strain index color-contour three-dimensional maps are shown. 3D left ventricular strain maps obtained from 10 subjects with dilated cardiomyopathy are presented. The heterogeneity of the regional contractile dysfunction as it relates to the regional expected norm is well demonstrated. Areas represented by the color red have regional contractile function that deviates from the expected norm to the same degree as nonviable myocardium in patients with ischemic cardiomyopathy.

Figure 11:
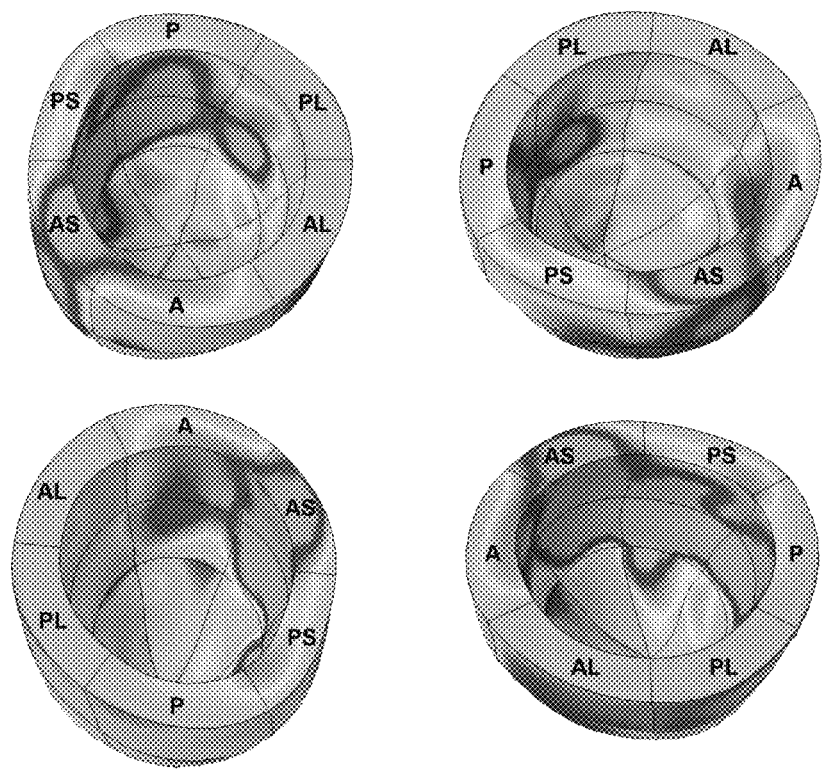
FIG. 11 is another series of left ventricular multiparametric myocardial strain color-contour images produced in accordance with the present invention.

Referring particularly to FIG. 11, composite (n=10) MRI-based multiparametric strain index color-contour maps of the left ventricle are shown. Multiparametric strain indices from each of 15,300 points for each of ten subjects with dilated cardiomyopathy are averaged together to create a single representation of the composite regional and transmural myocardial contractile function that can be anticipated in patients having this particular etiology to their cardiomyopathy. The regional heterogeneity of contractile dysfunction relative to the expected regional norm, including the predominant impairment of the ventricular septum, is demonstrated in this composite color contour map representing the entire group of non-ischemic, non-valvular dilated cardiomyopathy patients. In FIG. 11, the abbreviations AS=anteroseptal; A=anterior; AL=anterolateral; PL=posterolateral; P=posterior; and PS=posteroseptal.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing an image indicative of myocardial contractile function with a magnetic resonance imaging (MRI) system, the steps comprising:
   a) acquiring, with the magnetic resonance imaging (MRI) system, image data of a subject's heart;
   b) reconstructing images from acquired image data;
   c) calculating, from reconstructed images, a plurality of strain values at each of a plurality of points in the subject's heart;
   d) normalizing calculated strain values using values in a stored reference heart model, wherein the stored reference heart model includes, for each of the plurality of points in the subject's heart, a mean strain value ($\mu$) and a standard deviation value ($\sigma$) for each of the plurality of strain values, and wherein the mean strain values ($\mu$) and the standard deviation values ($\sigma$) are calculated using strain values from a plurality of other subjects having normal myocardial contractile function such that a normalization is performed relative to the plurality of other subjects having normal myocardial contractile function;

e) producing from normalized strain values an image indicative of myocardial contractile function; and f) combining normalized strain values at each of the plurality of points in the subject's heart to produce a multiparametric strain index for each point of the plurality of points in the subject's heart.

2. The method as recited in claim 1 in which the plurality of strain values includes circumferential strain, longitudinal strain, and minimum principal strain angle.

3. The method as recited in claim 1 in which step a) employs a tagging pulse sequence that produces a grid of lines in the images reconstructed in step b) and the strain values are calculated in step c) by measuring changes in the grid lines of images acquired at different cardiac phases.

4. The method as recited in claim 1 wherein a normalized strain ($X_n$) is calculated from the strain value (X) calculated in step c) according to the formula $$X_n = (X-\mu)/\sigma.$$

5. The method as recited in claim 4 wherein the image indicative of myocardial contractile function produced in step e) is an image of the subject's heart in which multiparametric strain index values are employed to modulate color at corresponding locations in a heart image.

6. The method as recited in claim 1 in which the normalized strain values are combined in step f) by averaging their values.

7. The method as recited in claim 1 in which the normalized strain values to be combined in step f) are weighted differently.

8. The method as recited in claim 1 which further includes:

g) defining a plurality of regions in the heart; and h) calculating a regional average strain index by averaging multiparametric strain indices at points within a region.

9. The method as recited in claim 1 wherein the image indicative of myocardial contractile function produced in step e) includes:

e) i) producing an image of a heart model; and e) ii) color coding pixels in the heart model image using multiparametric strain index values.

10. The method as recited in claim 1 in which steps a) through d) are repeated to produce second normalized strain values, and the image produced in step e) is produced using a difference between the normalized strain values and corresponding second normalized strain values.

11. The method as recited in claim 10 which further includes:

calculating a composite score by averaging the normalized strain values;

calculating a second composite score by averaging the corresponding second normalized strain values; and comparing the second composite score with the composite score to indicate a change in myocardial contractile function.

12. The method as recited in claim 1 which further includes:

g) calculating a composite score by averaging substantially all multiparametric strain index values.

13. The method as recited in claim 1, wherein combining normalized strain values comprises combining a normalized circumferential strain, a normalized longitudinal strain, and a normalized principal strain angle at each of the plurality of points in the subject's heart to produce the multiparametric strain index for each point of the plurality of points in the subject's heart.

14. The method as recited in claim 1, wherein calculating a plurality of strain values comprises calculating a plurality of a strain values at each of a plurality of points arranged in an evenly spaced grid.

15. A method for producing an image indicative of myocardial contractile function with a magnetic resonance imaging (MRI) system, the steps comprising:

a) acquiring, with the magnetic resonance imaging (MRI) system, image data of a subject's heart;

b) reconstructing images from acquired image data;

c) calculating, from reconstructed images, a plurality of strain values at each of a plurality of points in the subject's heart;

d) producing a normalized set of strain values by normalizing calculated strain values using values in a stored reference heart model, wherein the stored reference heart model includes, for each of the plurality of points in the subject's heart, a mean strain value ($\mu$) and a standard deviation value ($\sigma$) for each of the plurality of strain values, and wherein the mean strain values ($\mu$) and the standard deviation values ($\sigma$) are calculated using strain values from a plurality of other subjects having normal myocardial contractile function such that a normalization is performed relative to the plurality of other subjects having normal myocardial contractile function;

e) repeating steps a) through d) to produce a second set of normalized strain values;

f) combining the first set of normalized strain values at each of the plurality of points in the subject's heart to produce a first set of multiparametric strain indices;

g) combining the second set of normalized strain values at each of the plurality of points in the subject's heart to produce a second set of multiparametric strain indices; and h) producing an image using two sets of normalized strain values that is indicative of the change in myocardial contractile function.

16. The method as recited in claim 15 wherein step h) uses two sets of multiparametric strain indices to produce this image.

17. The method as recited in claim 16 in which step h) includes:

h) i) subtracting one set of multiparametric strain indices from another to produce a corresponding set of difference indices; and h) ii) producing an image of the heart in which the difference indices are employed to modulate color at corresponding locations in a heart image.

18. The method as recited in claim 15, wherein calculating a plurality of strain values comprises calculating a plurality of a strain values at each of a plurality of points arranged in an evenly spaced grid.

* * * * *